(12) United States Patent
Diao et al.

(10) Patent No.: US 12,135,452 B2
(45) Date of Patent: Nov. 5, 2024

(54) SINGLE FIBER ILLUMINATED LASER PROBE WITH HIGH-ANGLE ILLUMINATION OUTPUT

(71) Applicant: Alcon Inc., Fribourg (CH)

(72) Inventors: Chenguang Diao, Irvine, CA (US); Ronald T. Smith, Irvine, CA (US); Alireza Mirsepassi, Irvine, CA (US)

(73) Assignee: Alcon Inc., Fribourg (CH)

( * ) Notice: Subject to any disclaimer, the term of this patent is extended or adjusted under 35 U.S.C. 154(b) by 319 days.

(21) Appl. No.: 17/651,447

(22) Filed: Feb. 17, 2022

(65) Prior Publication Data

US 2022/0268990 A1    Aug. 25, 2022

Related U.S. Application Data

(60) Provisional application No. 63/152,412, filed on Feb. 23, 2021.

(51) Int. Cl.
*A61F 9/008*     (2006.01)
*G02B 6/02*      (2006.01)

(52) U.S. Cl.
CPC ............ *G02B 6/02* (2013.01); *A61F 9/00821* (2013.01); *A61F 2009/00863* (2013.01)

(58) Field of Classification Search
CPC .............................. G02B 6/02; A61F 9/00821
USPC ........................................................ 606/15
See application file for complete search history.

(56) References Cited

U.S. PATENT DOCUMENTS

| | | | |
|---|---|---|---|
| 5,995,686 A | 11/1999 | Hamburger et al. |
| 6,066,128 A | 5/2000 | Bahmanyar et al. |
| 8,398,240 B2 | 3/2013 | Smith |
| 8,480,279 B2 | 7/2013 | Papac et al. |
| 8,571,364 B2 | 10/2013 | Smith |
| 8,900,139 B2 | 12/2014 | Yadlowsky |
| 8,951,244 B2 | 2/2015 | Smith |
| 8,968,347 B2 | 3/2015 | McCollam |
| 9,308,128 B2 | 4/2016 | Smith |
| 9,402,643 B2 | 8/2016 | Auld |
| 9,561,085 B2 | 2/2017 | Yadlowsky |
| 10,245,181 B2 | 4/2019 | Diao |
| 10,278,785 B2 | 5/2019 | Mirsepassi |
| 10,639,198 B2 | 5/2020 | Farley |
| 10,859,748 B2 | 12/2020 | Mirsepassi et al. |
| 10,888,219 B2 | 1/2021 | Smith et al. |

(Continued)

FOREIGN PATENT DOCUMENTS

WO    2011102870 A1    8/2011

*Primary Examiner* — Nadia A Mahmood

(57) ABSTRACT

The present disclosure relates to a fiber and a laser probe assembly with a probe tip that houses the fiber. In certain aspects, the fiber includes a core, an outer cladding surrounding the core, and an end face at a proximal and/or distal end of the fiber. The core is configured to transmit a laser light beam while the core and the outer cladding are both configured to transmit an illumination light. In certain aspects, a surface area of the end face corresponding to a cross-section of at least the outer cladding is treated with a roughening or polishing process to modulate an illumination light output angle of the fiber. Using a fiber that is configured to transmit a laser light beam as well as a wide-angle illumination light allows for a more compact fiber and probe tip, allowing for medical procedures that require a narrower probe.

8 Claims, 11 Drawing Sheets

(56) References Cited

U.S. PATENT DOCUMENTS

| | | |
|---|---|---|
| 10,952,808 B2 | 3/2021 | Johnson |
| 11,109,938 B2 | 9/2021 | Horn et al. |
| 11,160,686 B2 | 11/2021 | Cook et al. |
| 2006/0184162 A1 | 8/2006 | Smith |
| 2008/0108981 A1* | 5/2008 | Telfair .................. A61B 18/24 |
| | | 606/4 |
| 2008/0108983 A1 | 5/2008 | Nadolski |
| 2008/0177257 A1 | 7/2008 | Smith et al. |
| 2009/0093800 A1 | 4/2009 | Auld |
| 2014/0180264 A1 | 6/2014 | Diao et al. |
| 2014/0200566 A1 | 7/2014 | Smith |
| 2015/0032190 A1 | 1/2015 | Acker |
| 2019/0175300 A1 | 6/2019 | Horn |
| 2020/0397614 A1 | 12/2020 | Diao et al. |
| 2021/0173143 A1 | 6/2021 | Diao et al. |
| 2021/0220077 A1 | 7/2021 | Bacher et al. |
| 2021/0255388 A1 | 8/2021 | Diao et al. |

* cited by examiner

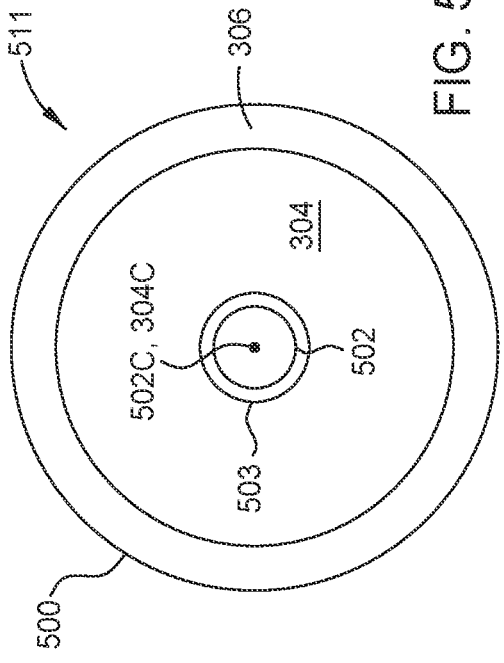
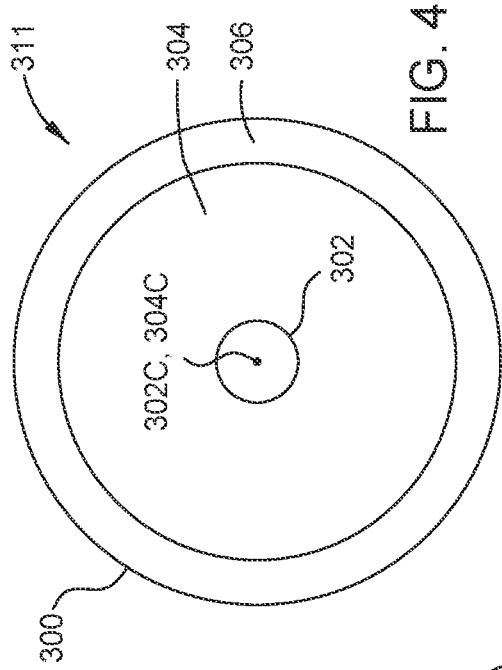
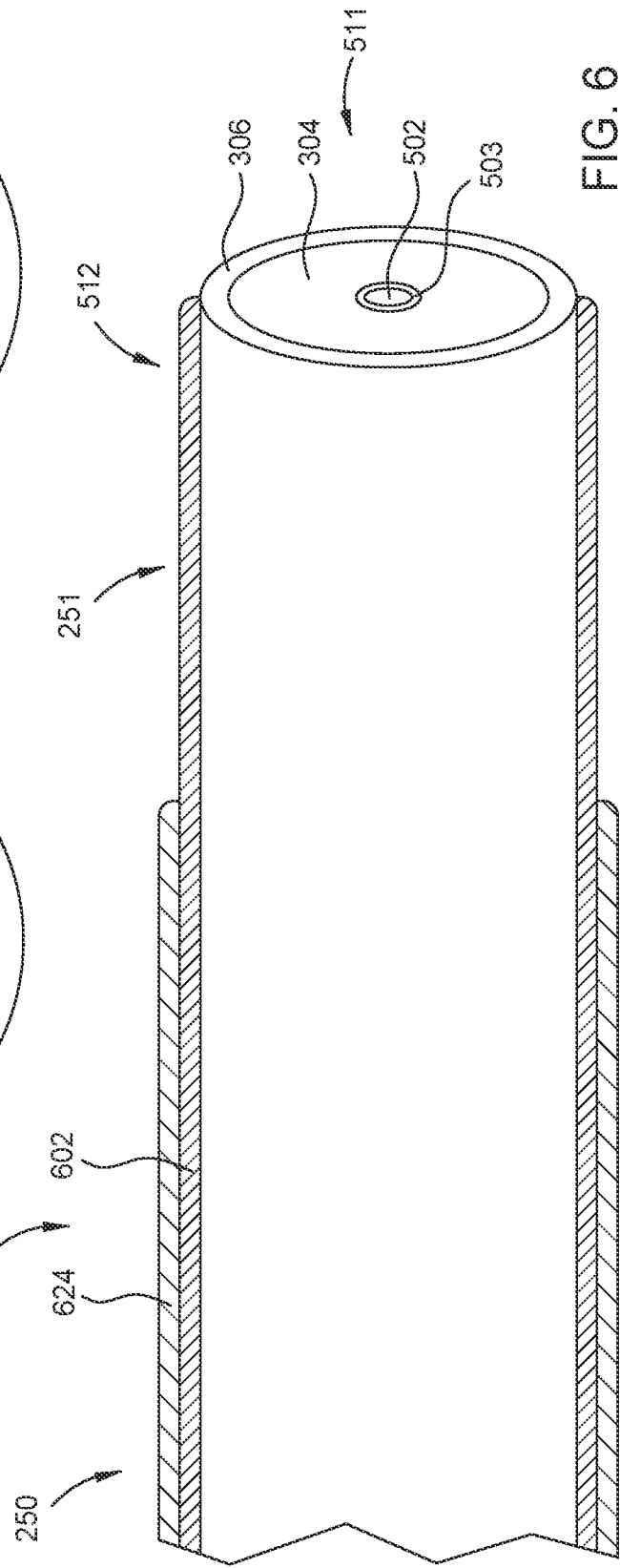

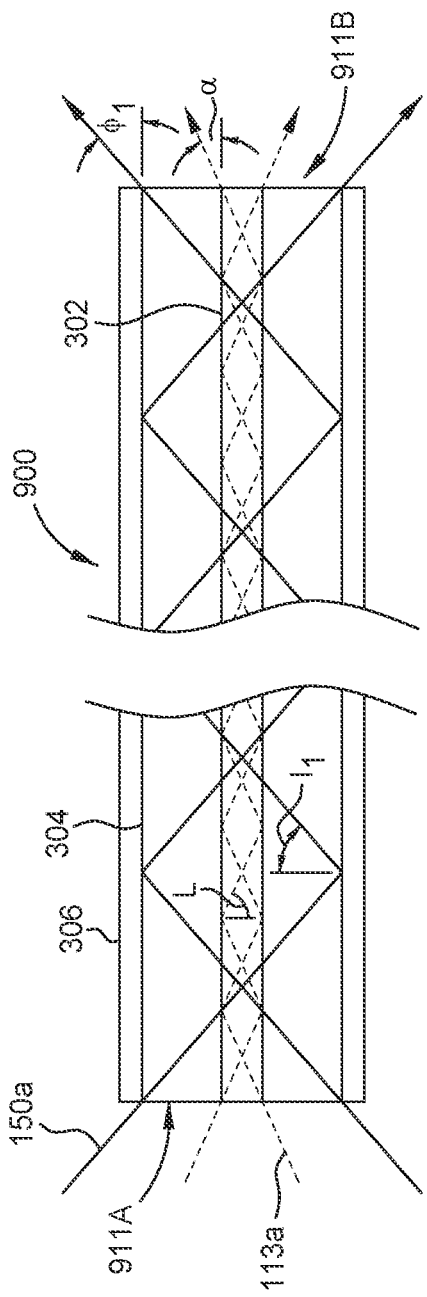
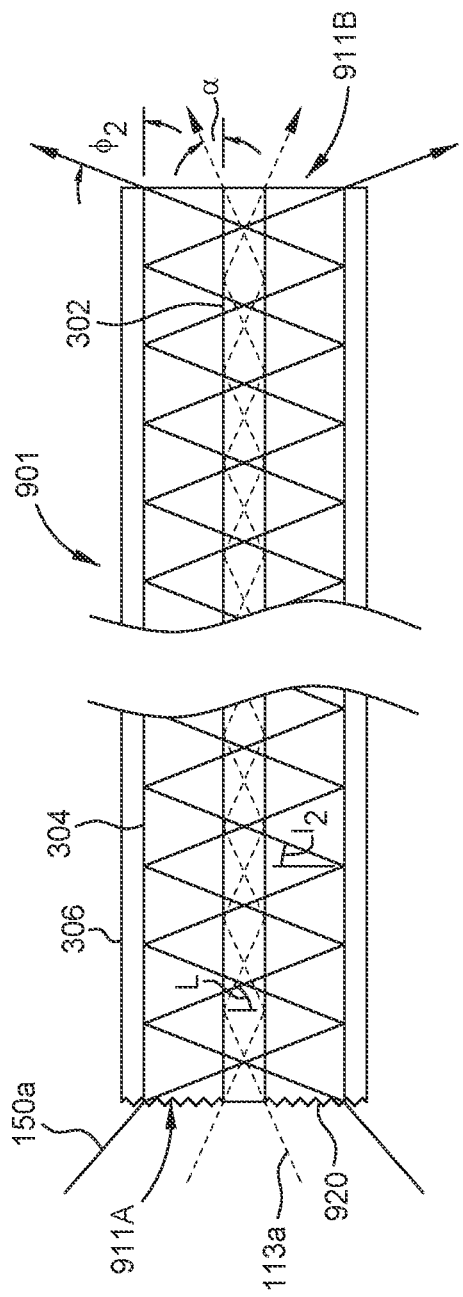

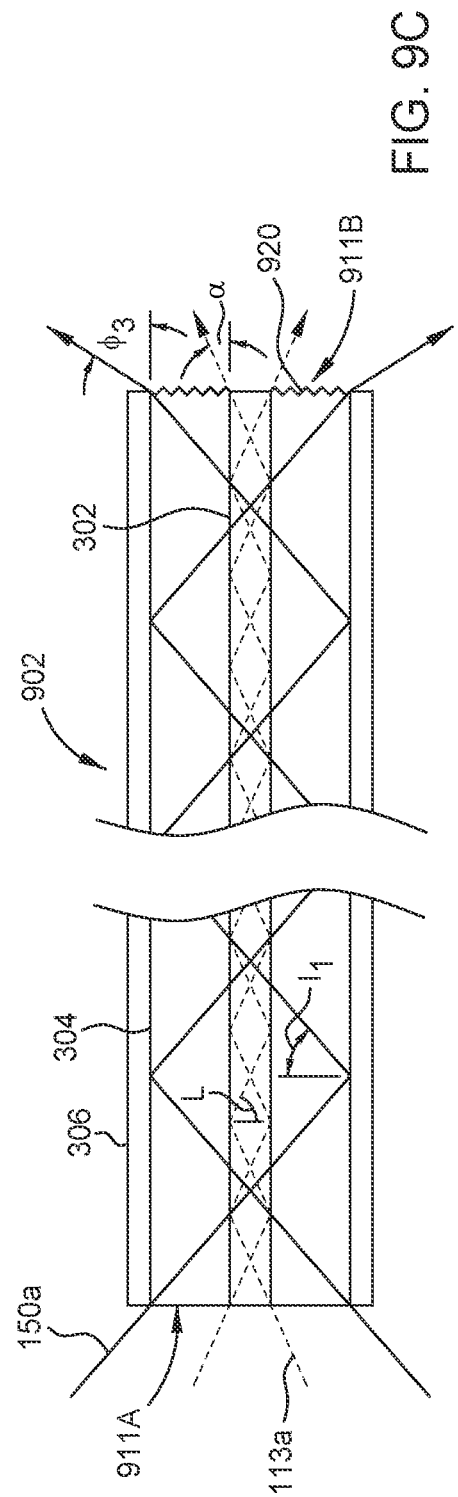

SINGLE FIBER ILLUMINATED LASER PROBE WITH HIGH-ANGLE ILLUMINATION OUTPUT

PRIORITY CLAIM

This application claims the benefit of priority of U.S. Provisional Patent Application Ser. No. 63/152,412 titled "SINGLE FIBER ILLUMINATED LASER PROBE WITH HIGH-ANGLE ILLUMINATION OUTPUT," filed on Feb. 23, 2021, whose inventors are Chenguang Diao, Ronald T. Smith and Alireza Mirsepassi, which is hereby incorporated by reference in its entirety as though fully and completely set forth herein.

FIELD

The present disclosure relates to small-gauge instrumentation for surgical procedures, and more specifically, to an optical fiber for transmitting both an illumination light and a laser light beam during ophthalmic surgical procedures.

BACKGROUND

In a wide variety of medical procedures, laser light is used to assist the procedure and treat patient anatomy. For example, in laser photocoagulation, a laser probe is used to cauterize blood vessels on the retina. Some laser probes include an optical fiber cable containing one fiber for delivering laser light to the surgical site, and a separate fiber for simultaneously delivering illumination light during an eye surgery procedure, for instance, during a bimanual operation. In such cases, one of the two fibers is connected to a laser source to deliver the laser beam, and the other fiber is connected to an illumination source for illumination light. The two fibers are then combined and tightly packed within a tube of the optical fiber cable to minimize the size of the optical fiber cable and, therefore, the size of the probe tip where the optical fiber cable is placed. Using a probe tip with a smaller gauge size is advantageous because it facilitates minimization of incision size on the eye (for example, mini-invasive eye surgery), and helps patients recover faster post-surgery.

However, an optical fiber cable containing a laser fiber as well as an illumination fiber can only be made so narrow, because there must be room for both the illumination fiber and the laser fiber to be placed side-by-side in the tube. Narrowing of the two fibers themselves results in lower laser coupling efficiency and insufficient illumination to perform the medical procedure. Further, the fabrication of the probe for integrating the two separate fibers (where one fiber is for the laser beam, and the other fiber is for the illumination light), is complicated, and the cost of manufacturing the probe is high. In addition, the thermal robustness of the probe is an issue at high laser powers due to the plastic fiber used for illumination light, and the adhesive used to bind the fibers together at the distal end of the probe.

Therefore, what is needed in the art is an improved single fiber illuminated laser probe having a high-angle illumination output while maintaining high laser coupling efficiency.

SUMMARY

According to certain embodiments, a laser probe assembly is provided, including a probe body shaped and sized for grasping by a user, and a probe tip housing a fiber having a proximal end face and a distal end face opposite the proximal end face. The fiber further includes a core, an outer cladding circumferentially surrounding the core, and a coating circumferentially surrounding the outer cladding. The core is configured to transmit a laser light beam and an illumination light. The outer cladding is configured to transmit an illumination light. At least a surface area of the proximal end face or the distal end face of the fiber corresponding to the outer cladding is roughened.

According to certain embodiments, a fiber is provided, including a proximal end face at a proximal end of the fiber and a distal end face at a distal end of the fiber. The fiber further includes a core, an outer cladding circumferentially surrounding the core, and a coating circumferentially surrounding the outer cladding. The core is configured to transmit a laser light beam and an illumination light. The outer cladding is configured to transmit the illumination light. At least a surface area of the proximal end face or the distal end face of the fiber corresponding to the outer cladding is roughened.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

FIG. 4 illustrates a cross-sectional front view of a fiber end face, in accordance with certain embodiments of the present disclosure.

FIG. 5 illustrates a cross-sectional front view of a fiber end face with an inner cladding, in accordance with certain embodiments of the present disclosure.

FIG. 6 illustrates a partial cross-sectional view of a probe tip and a fiber, in accordance with certain embodiments of the present disclosure.

FIGS. 9A-9C illustrate schematic cross-sectional views of a fiber, in accordance with certain embodiments of the present disclosure.

FIG. 10 illustrates a flow diagram of a method of forming a fiber, in accordance with certain embodiments of the present disclosure.

To facilitate understanding, identical reference numerals have been used, where possible, to designate identical elements that are common to the Figures. It is contemplated that elements and features of one embodiment may be beneficially incorporated in other embodiments without further recitation.

DETAILED DESCRIPTION

Figure 1A:
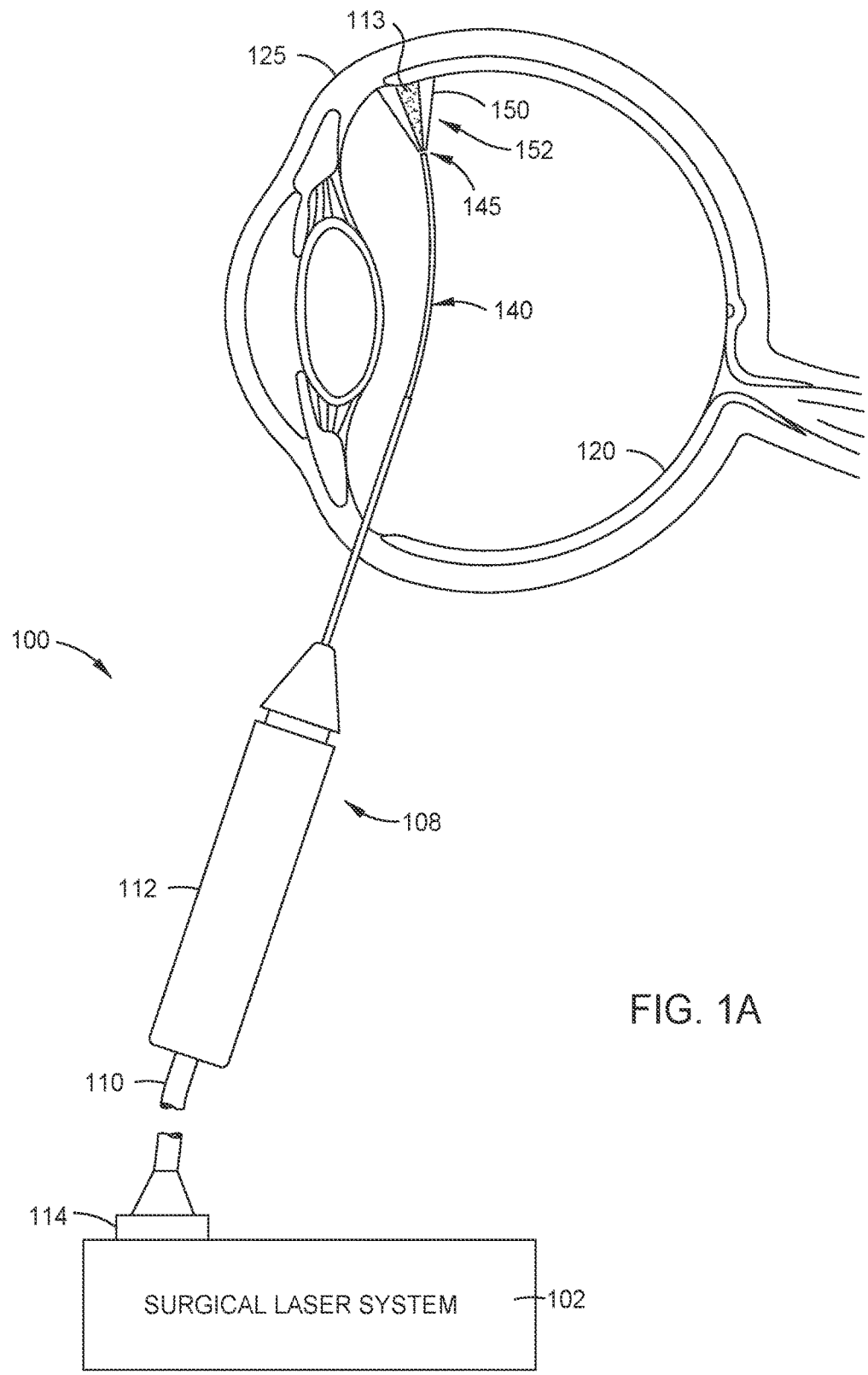
FIG. 1A illustrates a plan view of a system for generating laser and illumination light beams for delivery to a surgical target, in accordance with certain embodiments of the present disclosure.

In the following description, details are set forth by way of example to facilitate an understanding of the disclosed subject matter. It should be apparent to a person of ordinary skill in the field, however, that the disclosed implementations are exemplary and not exhaustive of all possible implementations. Thus, it should be understood that reference to the described examples is not intended to limit the scope of the disclosure. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

Embodiments of the present disclosure generally relate to fibers and laser probe assemblies for surgical procedures. A fiber includes a core that transmits a laser light beam, and the core and an outer cladding surrounding the core that transmit illumination light. A laser probe assembly includes a fiber, and the laser probe assembly allows the user to direct a laser light beam and illumination light simultaneously in a single fiber. Furthermore, one or more end faces (e.g., surfaces) of the fiber may be treated to increase the illumination output (e.g., spreading) angle of the fiber. Generally, the end faces may be treated at least one of two ways to attain such an effect. In certain examples, one or more end faces of the fiber are treated with a roughening process to increase illumination light scattering characteristics of the treated end face(s). In certain examples, one or more end faces are angled by a polishing process to increase illumination light scattering characteristics of the treated end face(s). The end face treatment, whether it includes roughening and/or angling, may be limited to a surface area of the one or more end faces corresponding to the outer cladding, thus only affecting the propagation of illumination light from the fiber. Accordingly, the illumination output angle of the fiber may be increased, while laser beam efficiency and laser beam spot size remain unaffected to maintain photocoagulation performance. The combination of the transmission of laser light and illumination light in the same fiber with treated end-surface(s) results in a more compact optical fiber cable having improved illumination, allowing for enhanced visibility during medical procedures that require a smaller gauge probe. Embodiments of the disclosure may be especially useful for, but are not limited to, a fiber that can transmit both laser light and wide-angle illumination light.

As used herein, the term "about" may refer to a +/−10% variation from the nominal value. It is to be understood that such a variation can be included in any value provided herein.

FIG. 1A illustrates a plan view of a system 100 for generating an illumination beam as well as a laser light beam for delivery to a surgical target, in accordance with certain embodiments of the present disclosure. As shown, system 100 includes a surgical laser system 102 and a probe 108. The system 100 produces an illumination beam 150 and a laser light beam 113 to be delivered, for example, to the retina 120 of a patient's eye 125.

The surgical laser system 102 includes a number of laser light sources (e.g., one or more laser light sources) for generating laser light beams that can be used during an ophthalmic procedure. Accordingly, the surgical laser system 102 may be an ophthalmic surgical laser system configured to generate a laser light beam 113 (e.g., a surgical treatment beam). A user, such as a surgeon or other medical practitioner, can control the surgical laser system 102 (e.g., via a foot switch, voice commands, surgical console, etc.) to fire the laser light beam 113 to treat patient anatomy, e.g., perform photocoagulation. In some instances, the surgical laser system 102 includes a port, and the illumination beam 150 and the laser light beam 113 can be emitted through the port in the surgical laser system 102.

System 100 can deliver the laser light beam 113 and the illumination light 150 from the port to a probe 108 via a fiber contained in an optical fiber cable 110, a proximal end of which couples to the port of the surgical laser system 102 through port adapter 114. As shown, probe 108 includes a probe body 112, a probe tip 140, and a distal end 145 of the probe tip. In operation, a laser light source of surgical laser system 102 generates the laser light beam 113, while an illumination light source generates the illumination light 150. The surgical laser system 102 multiplexes the laser light beam 113 and the illumination light 150 into a multiplexed beam 152. The multiplexed beam 152 is directed to a lens of the surgical laser system 102 to focus the multiplexed beam onto an interface plane of a proximal end of the fiber within the optical fiber cable 110, such that the multiplexed beam is transmitted along an entire length of the fiber. The interface plane of the proximal end of the fiber is exposed by a ferrule inserted into a port adapter 114 through which optical fiber cable 110 connects to the surgical laser system 102.

The multiplexed beam 152 is transmitted by the fiber to the probe 108 disposed at a distal end of the optical fiber cable 110. The multiplexed 152 beam exits the probe tip 145 and is projected onto the retina 120. Thus, the surgical laser system 102 is configured to deliver the multiplexed beam 152 to the retina 120 through the fiber of the optical fiber cable 110. The multiplexed beam 152 includes both the laser light beam 113 for the surgical procedure and illumination light 150 to aid the user in the procedure, although the beam associated with the laser light beam 113 is narrower.

Note that, herein, a distal end of a component refers to the end that is closer to a patient's body, or where the laser light beam 113 is emitted out of the laser probe 112. On the other hand, the proximal end of the component refers to the end that is facing away from the patient's body or in proximity to, for example, the surgical laser source 102.

Figure 1B:
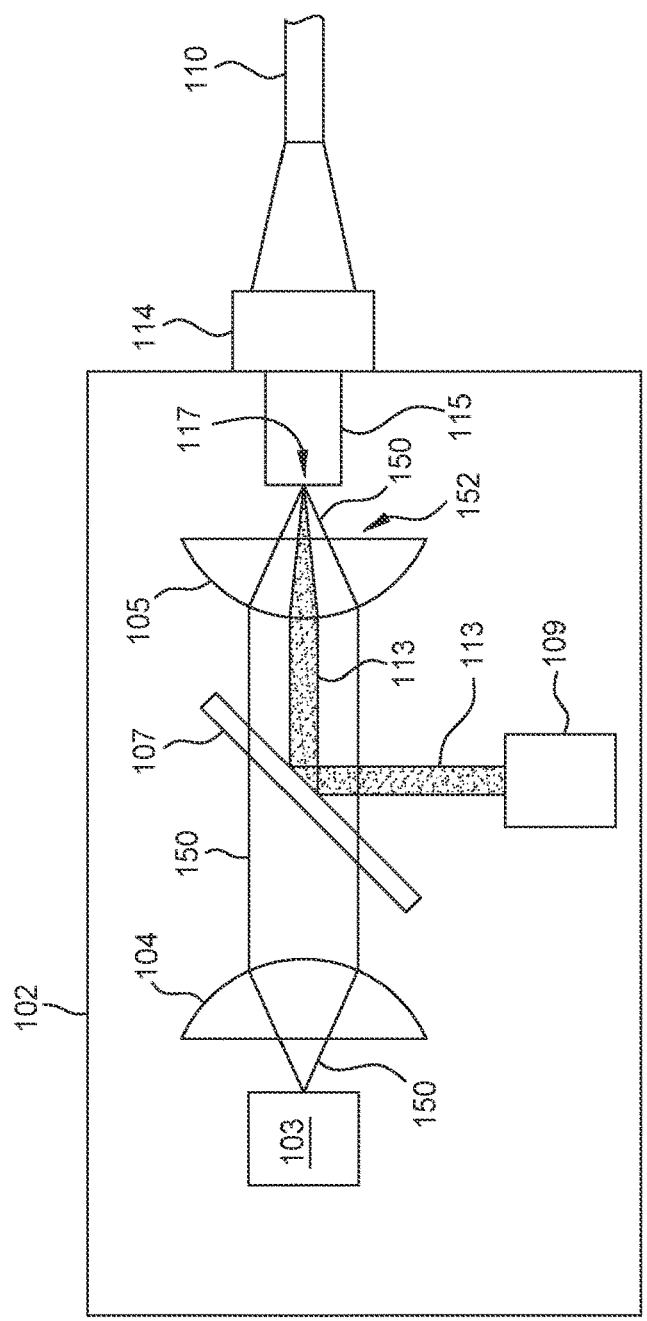
FIG. 1B illustrates a schematic plan view of a surgical laser system, in accordance with certain embodiments of the present disclosure.

FIG. 1B illustrates a plan view of a surgical laser system 102, in accordance with certain embodiments of the present disclosure. As shown, the surgical laser system 102 includes a first lens 104 (e.g., collimating lens), a beam splitter 107, an optical fiber cable 110, a second lens 105 (e.g., focusing lens), an illumination light source 103, and a laser light source 109. The beam splitter 107 is downstream from the first lens 104, the second lens 105 is downstream from the beam splitter 107, and the optical fiber cable 110 is downstream from the second lens 105.

The illumination light source 103 emits an illumination light 150. The illumination light 150 can be any spectrum of light, including, but not limited to, visible light or white light. The illumination light source 103 can be a light-emitting diode (LED), a broadband laser, or an incoherent light source such as a xenon or halogen light source. The illumination light 150 is collimated by the first lens 104 such that the illumination light 150 is transformed into a beam of light with parallel rays, as shown. The first lens 104 can be any lens, including a plano-convex or biconvex lens. The beam splitter 107 allows the illumination light 150 to pass through the beam splitter 107 with a small fraction of the light reflected off the beam splitter. The illumination light 150 is then focused by the second lens 105, as shown. The second lens 105 can be any lens used to focus light, including a plano-convex or biconvex lens. The illumination light 150 and laser beam 113 are focused and incident on the optical fiber cable 110 as a multiplexed beam 152, which is described in greater detail below.

The second lens 105 focuses the multiplexed beam 152 into an interface plane of a proximal end of a fiber that is contained within the optical fiber cable 110. As shown, optical fiber cable 110 is coupled to the surgical laser system 102 through port adapter 114, which receives a ferrule 115 that exposes an interface plane of the proximal end of the fiber, which is contained within optical fiber cable 110. More specifically, the interface plane of the proximal end of the fiber is exposed through an opening 117 of ferrule 115. The second lens 105 focuses multiplexed beam 152 onto an interface plane of the proximal end of the fiber such that the multiplexed beam is propagated through the fiber to the distal end of a surgical probe (e.g., probe 108 of FIG. 1A) that is coupled to cable 110.

The optical fiber cable 110 may include a fiber (e.g., fiber 300, a portion 311 of which is shown in FIG. 4) having a core, an outer cladding, and a coating in some embodiments. In such embodiments, the second lens 105 is configured to focus the illumination light 150 onto both the core and the outer cladding, in which case both the outer cladding and the core transmit the illumination light 150.

In yet some other embodiments, optical fiber cable 110 may include a fiber (e.g., fiber 500, whose portion 511 is shown in FIG. 5) having a core, an inner cladding, an outer cladding, and a coating. In such embodiments, the illumination light 150 is focused on the core, the inner cladding, and the outer cladding in which case the core, the inner cladding, and outer cladding all transmit the illumination light 150.

A laser light source 109 emits a laser light beam 113. The laser light beam 113 can have any desired wavelength, such as from about 532 nm (nanometers) to about 635 nm. The laser light source 109 can emit a variety of wavelengths desired by the user. The laser light beam 113 is reflected by the beam splitter 107 onto focusing lens 105. The laser light beam 113 is then focused by the second lens 105 onto an interface plane of the proximal end of optical fiber cable 110, as part of the multiplexed beam 152. The laser light beam 113 is transmitted by the core of the optical fiber cable 110. The surgical laser system 102 provides both the illumination light 150 and the laser light beam 113 to the optical fiber cable 110 as the multiplexed beam 152. Thus, a single fiber in the optical fiber cable 110, including a core and an outer cladding, is capable of transmitting both the laser light beam 113 (through the core) and illumination light 150 (through the outer cladding and the core) in the same fiber.

Figure 2:
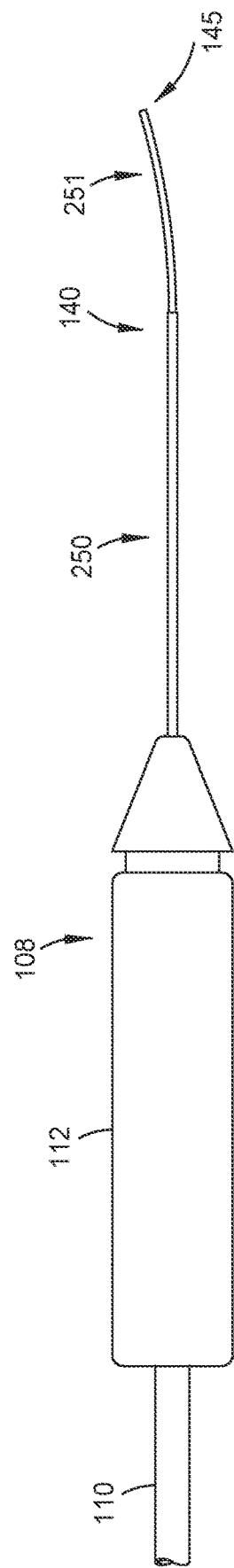
FIG. 2 illustrates a plan view of a probe, in accordance with certain embodiments of the present disclosure.

FIG. 2 illustrates a plan view of the probe 108, in accordance with certain embodiments of the present disclosure. As described above, the probe 108 includes a hand piece or probe body 112 shaped and sized for grasping by a user. Extending from the probe body 112 is the probe tip 140 with a distal end 145. The optical fiber cable 110 typically comprises a fiber (e.g., fiber 300 of FIG. 3, fiber 500 of FIG. 5, etc.) surrounded by a polyvinyl chloride (PVC) tube for protecting the fiber during handling. The fiber extends through the probe body 112 and into the probe tip 140. The multiplexed beam 152 (shown in FIG. 1A) emanates from the distal end of the fiber and, thereby, the distal end 145 of the probe tip 140 onto the retina. In some embodiments, the probe tip 140 comprises a first straight portion 250 and a second curved portion 251. The first straight portion 250 includes a sleeve of the probe tip, and the second curved portion 251 includes a tube surrounding the fiber. The embodiment of FIG. 2 is merely shown as an example. In other examples, a probe tip may include the first straight portion 250 and second curved portion 251, but without a sleeve. A variety of other configurations are also possible and are not outside the scope of this disclosure, as one of ordinary skill in the art can appreciate.

Figure 3A:
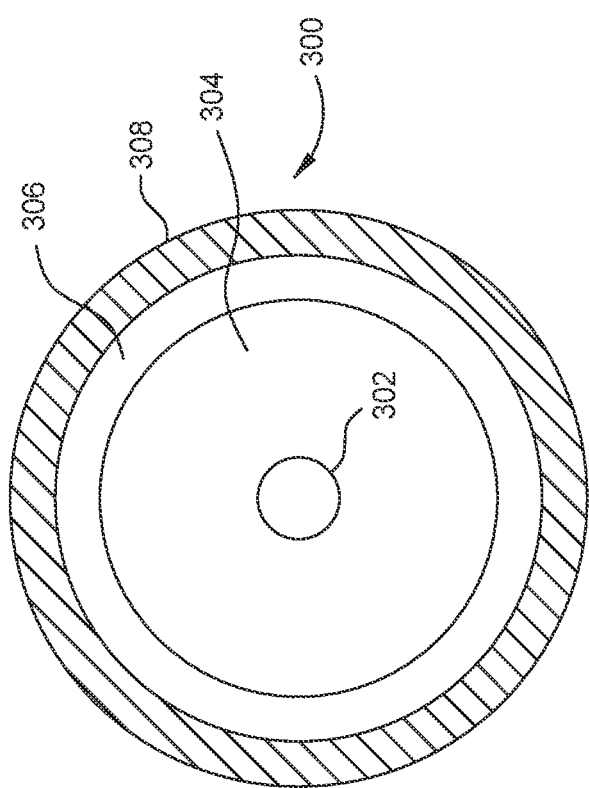
FIGS. 3A-3B illustrate different views of a fiber, in accordance with certain embodiments of the present disclosure
Figure 3B:
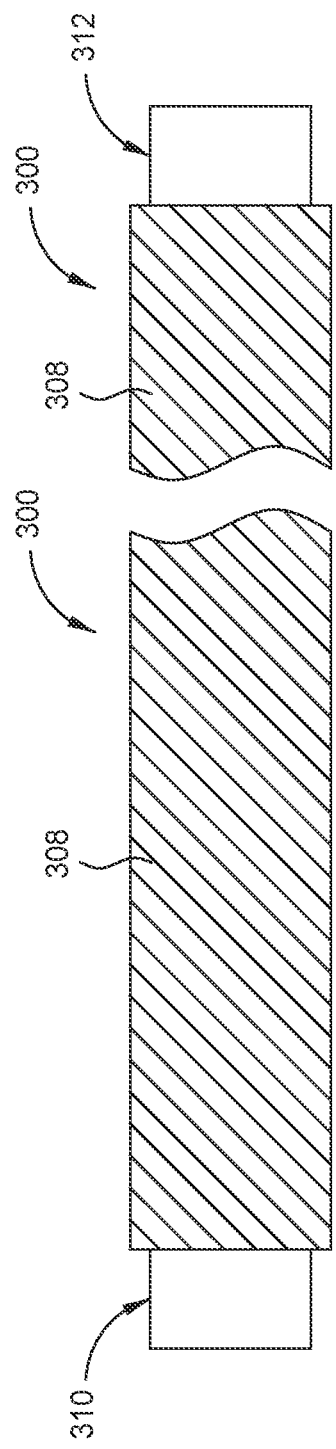

FIGS. 3A-3B illustrate a fiber 300, in accordance with certain embodiments of the present disclosure. As shown, the fiber 300 includes a core 302, an outer cladding 304, a coating 306 (e.g., a low refractive index cladding), and a buffer 308. The buffer 308 can include plastic, such as ethylene tetrafluoroethylene (ETFE). The buffer 308 is stripped at proximal end 310 of the fiber 300 so that the proximal end 310 of the fiber 300 can be inserted to the ferrule. The buffer is also stripped at distal end 312 of the fiber 300 so that the distal end 312 of the fiber 300 can be inserted into probe tip 140, according to some embodiments.

FIG. 4 illustrates a cross-sectional front view of an end face 311 of fiber 300, in accordance with certain embodiments of the present disclosure. The end face 311 may be a proximal or distal end face of the fiber 300, e.g., located at either proximal end 310 or distal end 312. The end face 311 includes a core 302 disposed in an outer cladding 304, and the outer cladding 304 includes a material that can include fused silica. Note, however, that the end face 311 does not include the buffer 308, as the buffer 308 has been stripped from around the ends 310, 312. Laser light beam 113 (shown in FIG. 1A) provided by a laser light source of the surgical laser system 102 is directed into the core 302 of the fiber 300. Thus, the core 302 conducts the laser light beam 113 along the length of the fiber 300. Both core 302 and outer cladding 304 may include fused silica. However, the core 302 is doped with a dopant that increases the index of refraction of the core 302. Therefore, the refractive index of the core 302 is greater than the refractive index of the outer cladding 304, such that the laser light beam 113 traveling along the core 302 is contained within the core 302 and prevented from escaping from the core 302 into the outer cladding 304. In one example, the dopant can include germanium (Ge). The core 302 and the outer cladding 304 may both transmit illumination light 150 (shown in FIG. 1A) from the surgical laser system 102. Thus, a single fiber including the core 302 and the outer cladding 304 is capable of simultaneously transmitting both the laser light beam 113 (through the core 302) and illumination light 150 (through the outer cladding 304 and the core 302). In addition, using fused silica for transmitting the illumination light 150, such as in fiber 300 of FIG. 3 or fiber 500 of FIG. 5, results in a more thermally stable fiber as compared to a conventional illumination fiber that is made of traditional plastic, and there is no need to use adhesive to bond two fibers, which makes the fiber more thermally robust.

A coating 306 is formed over the outer cladding 304. Note that the coating 306 may also be referred to as a cladding 306. In some instances, the coating 306 is a hard polymer coating. In other instances, the coating 306 is formed from other materials, such as acrylate. The refractive index of the coating 306 is less than the refractive index of the outer cladding 304, such that the illumination light 150 traveling along the outer cladding 304 is contained within the outer cladding 304 and prevented from escaping from the outer cladding 304 into the coating 306. In certain embodiments, the numerical aperture (NA) between the outer cladding 304 and the coating 306 is greater than about 0.5 to provide the wide illumination required in some surgical cases.

FIG. 5 illustrates a cross-sectional front view of an end face 511 of another fiber 500 with an inner cladding 503, in accordance with certain embodiments of the present disclosure. The end face 511 may be located at either the proximal end or distal end of the fiber 500, where the fiber's buffer has been stripped. In FIG. 5, the inner cladding 503 surrounds a core 502 and the outer cladding 304 surrounds the inner cladding 503. The inner cladding 503 can include fused silica doped with dopants, the dopants including fluorine, chlorine, boron, or any combination of the above, according to some embodiments. The dopants change the optical properties of the inner cladding 503, for example, the refractive index. In certain embodiments, the NA between the core 502 and the inner cladding 503 is from about 0.20 to about 0.30, such as about 0.22. The inner cladding 503 keeps the laser light beam 113 from entering the outer cladding 304 by causing partial or total internal reflection of the laser light beam 113, thus keeping the laser light beam 113 in the core 502. As described above, in the example of FIG. 5, the illumination light 150 is focused by the surgical laser system onto core 502, inner cladding 503, and the outer cladding 304 while the laser light beam 113 is focused on core 502.

Referring to FIGS. 4 and 5, in certain embodiments, the diameter of the cores 302, 502 is from about 70 μm to about 80 μm, the outer diameter of the outer cladding 304 is from about 290 μm to about 300 μm, and the outer diameter of the coating 306 is from about 320 μm to about 330 μm. The location of the centers 302c, 502c of the cores 302, 502 is approximately the same location as the center 304c of the outer cladding 304, according to one embodiment.

FIG. 6 illustrates a partial cross-sectional view of a probe tip 140, in accordance with certain embodiments of the present disclosure. A distal end 512 of a fiber, e.g., fiber 500, is partially surrounded by the tube 602, and the tube is surrounded by the sleeve 624 of the probe tip 140. The tube 602 can include any suitable material, for example, Nitinol, nickel titanium, stainless steel, MP35N (e.g., a nickel-cobalt base alloy), or other alloys. The sleeve 624 can include, for example, stainless steel. In the example of FIG. 6, the distal end 512 of the fiber and the distal end of the tube 602 surrounding the fiber extend beyond the distal end of the sleeve 624 of the probe tip 140. Thus, the first straight portion 250 of the probe tip 140 includes the sleeve 624, whereas the second curved portion 251 of the probe tip does not include the sleeve, although the distal end 512 is still surrounded by the tube 602 in the second curved portion. In other embodiments, the sleeve 624 extends to cover the entire distal end 512 throughout the probe tip 140. In other embodiments, the probe tip 140 includes the tube 602 and the sleeve 624 is not included. Although the distal end 512 illustrated in FIG. 6 includes the inner cladding 503, the optical fiber cable could instead resemble the embodiment in FIG. 4 (which does not include the inner cladding), without any loss of generality. As described above, the embodiment of FIG. 6 is merely shown as an example. One of ordinary skill in the art can appreciate other embodiments with different configurations (e.g., a completely straight probe tip, or a probe tip with a distal end that is flush with the distal ends of the fiber 500 and tube 602) which are also not outside the scope of this disclosure.

Figure 7:
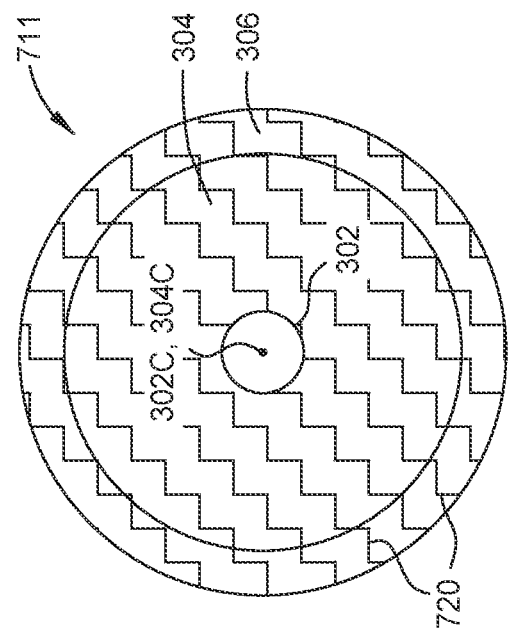
FIG. 7 illustrates a cross-sectional front view of a fiber end face, in accordance with certain embodiments of the present disclosure.

FIG. 7 illustrates a cross-sectional front view of an end face 711 of a fiber, in accordance with certain embodiments of the present disclosure. The end face 711 may be a distal and/or proximal end face of the fiber 300, which is partially exposed to an end face roughening treatment to increase an illumination light output angle of the fiber. The end face 711, similar to the end face 311 depicted in FIG. 4, includes core 302 circumferentially surrounded by outer cladding 304, and the outer cladding 304 circumferentially surrounded by coating 306. As shown, a surface area of the end face 711 corresponding to a cross-section of the outer cladding 304 and/or the coating 306 is at least partially roughened or coarsened (represented by hatch marks 720), while a surface area of the end face 711 corresponding to a cross-section of at least the core 302 is substantially smooth. The roughened surface area may be formed during a manufacturing process in which the end face 711 is selectively exposed to a particle abrasion treatment, described in more detail below. The particle abrasion treatment creates a surface area with increased light scattering characteristics. The smooth (e.g., flat) surface area, however, is left untreated during the aforementioned manufacturing process to ensure a substantially uniform surface plane, thus maintaining the light transmission properties thereof. In certain embodiments, the smooth or untreated surface area has a diameter that is about the same or slightly larger than a diameter of the core 302.

As described above, laser light, such as laser light beam 113, is propagated within the core 302, while illumination light, such as illumination light beam 150, is propagated within both the core 302 and outer cladding 304. Accordingly, by roughening the surface area of the end face 711 corresponding to the cross-section of the outer cladding 304 and/or the coating 306, the angular spread of the illumination light at the end face 711 is increased or widened, thus increasing the overall illumination light output angle of the fiber. In certain embodiments, the illumination light output angle of a fiber having at least one treated end face 711 is increased between about 0.05 NA and about 0.25 NA, such as between about 0.1 and about 0.2 NA, as compared to a fiber having both end faces left untreated. Furthermore, by leaving the surface area of the end face 711 corresponding to the cross-section of the core 302 substantially smooth, laser beam efficiency and spot size of the laser light beam 113, which is propagated only through the core 302, remains unaffected, thus maintaining photocoagulation efficiency while improving the illumination light spreading angle.

Figure 8:
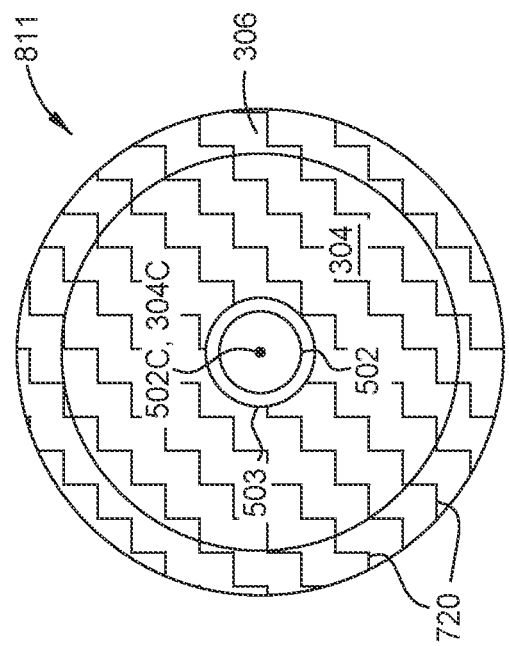
FIG. 8 illustrates a cross-sectional front view of a fiber end face with an inner cladding, in accordance with certain embodiments of the present disclosure.

FIG. 8 illustrates a front view of an end face 811 of another fiber partially exposed to an end face roughening treatment to improve the illumination light output angle of the fiber, in accordance with certain embodiments of the present disclosure. The end face 811 may be a distal or proximal end face of the fiber 500, and includes inner cladding 503 circumferentially surrounding core 502, an outer cladding 304 circumferentially surrounding the inner cladding 503, and a coating 306 circumferentially surrounding the outer cladding 304. As shown, a surface area of the end face 811 corresponding to a cross-section of the outer cladding 304 and/or the coating 306 is exposed to a roughness treatment (represented by hatch marks 720) to increase the illumination light angular spread thereof. The surface area of the end face 811 corresponding to a cross-section of at least the core 502 and the inner cladding 503, however, is left substantially smooth or untreated to maintain the laser beam efficiency and spot size of the laser light beam 113 propagated within the core 502. In certain embodiments, the diameter of the smooth or untreated surface area is substantially the same or larger than a diameter of the inner cladding 503.

In certain embodiments, the roughened surface areas of the end faces 711, 811 comprise features having a depth or amplitude between about 1.5 μm and about 6 In certain embodiments, the roughened surface areas account for at least about 50% of the total surface areas of the end faces 711, 811, such as at least about 80% of the total surface areas, such as at least about 90% of the total surface areas thereof.

For further clarification, FIGS. 9A-9C illustrate schematic cross-sectional views of illumination light and laser light propagating through proximal end faces 911A and distal end faces 911B of several fibers, similar to fibers 300 and 500 described above. FIG. 9A illustrates a fiber 900 wherein neither the proximal end face 911A nor the distal end face 911B are roughened. As depicted, laser light beam rays 113*a* enter the core 302 at the proximal end face 911A, reflect within the core 302 having a minimum angle of incidence L, and exit the core 302 at the distal end face 911B with an output angle α relative to a central axis of the fiber. Simultaneously, illumination light rays 150*a* enter the outer cladding 304 at the proximal end face 911A, reflect within the outer cladding 304 having a minimum angle of incidence $I_1$, and exit the outer cladding 304 at the distal end face 911B with an output angle $\varphi_1$ relative to a central axis of the fiber.

FIG. 9B illustrates a fiber 901 wherein a surface area of the proximal end face 911A corresponding to a cross-section of the outer cladding 304 is roughened (represented by sawtooth edge 920), causing diffuse scattering (e.g., increased angular spread) of the illumination light rays 150*a* that pass therethrough and enter the fiber. The diffusely scattered illumination rays 150*a* have a minimum angle of incidence $I_2$ within the outer cladding 304 that is smaller than the angle $I_1$, and thus exit the outer cladding 304 with an output angle $\varphi_2$ greater than output angle $\varphi_1$. The laser light rays 113*a* entering and propagating through the core 302, however, maintain the minimum angle of incidence L and thus, also maintain the output angle α, resulting in preserved laser beam quality.

FIG. 9C illustrates a fiber 902 wherein a surface area of the distal end face 911B corresponding to a cross-section of the outer cladding 304 is roughened (represented by sawtooth edge 920). Accordingly, the illumination light rays 150*a* reflecting within the outer cladding 304 have the same minimum angle of incidence $I_1$ as in FIG. 9A, but the illumination light rays 150*a* exit the outer cladding 304 at the distal end face 911B with an output angle $\varphi_3$ greater than output angle $\varphi_1$ as a result of diffuse scattering caused by the roughened surface. Similar to FIG. 9B, the laser light rays 113*a* propagating through the core 302 maintain the minimum angle of incidence L and the output angle α, since neither surface area at the distal or proximal end face 911A, 911B corresponding to the core 302 is roughened. Accordingly, similar to FIG. 9B, the angular spread of the illumination light rays 150*a* at the distal end face 911B of the fiber 902 is increased while laser beam spot size and efficiency are preserved.

It should be noted, however, that although only one end face of the fibers in each of FIGS. 9B and 9C is roughened, in certain embodiments, both end faces of a fiber may be roughened to achieve a desired illumination light output angle of the fiber. Furthermore, each end face of a fiber may be roughened to a different level or degree of roughness. The difference or delta in level of roughness between end faces may facilitate higher angular spread of illumination light as compared to having a single roughened end face or having two end faces with similar roughness levels. In certain examples, the distal end face is roughened to a greater degree than the proximal end face for higher output angular spread in air and saline mediums as compared to only roughening the distal end face, while also maintaining illumination light throughput similar to roughening of only the proximal end face.

Figure 11C:
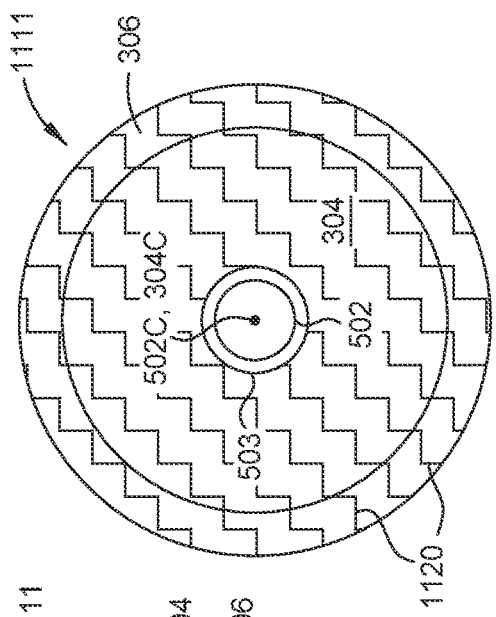
FIGS. 11A-11C illustrate different states of a fiber corresponding to the different operations of the method of FIG. 10, in accordance with certain embodiments of the present disclosure.
Figure 11B:
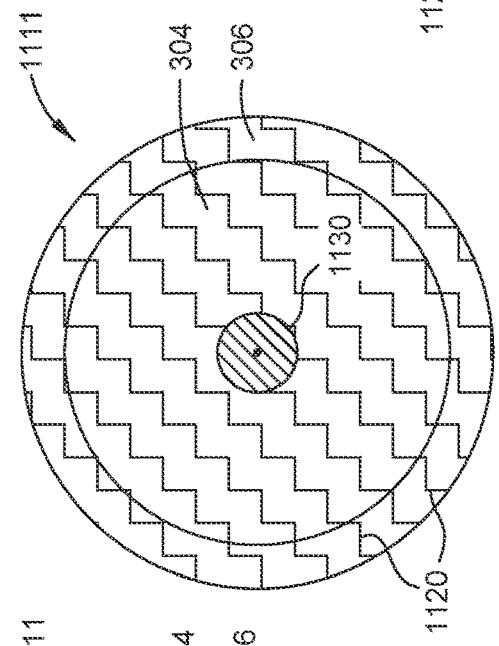
Figure 11A:
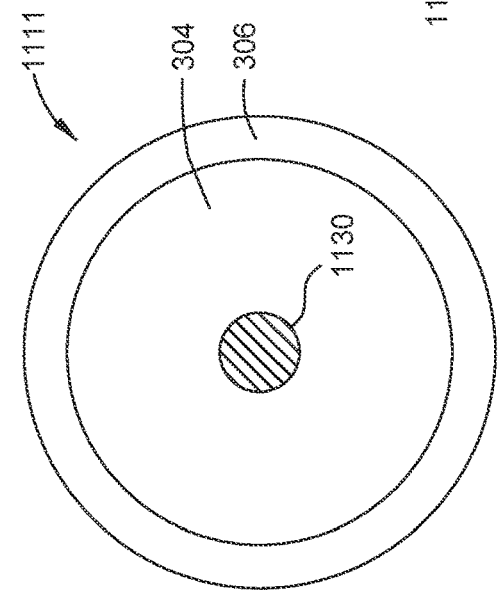

FIG. 10 illustrates a flow diagram of a method 1000 for treating an end face of a fiber to increase an illumination light output angle thereof, in accordance with certain embodiments of the present disclosure. FIGS. 11A-11C schematically illustrate front views of an end face 1111 of a fiber at different stages of the method 1000 represented in FIG. 10. Therefore, FIGS. 10 and 11A-11C are herein described together for clarity.

The method 1000 may be utilized to form the end faces 711, 811 described above. In certain embodiments, only one of the distal or proximal end faces of the fiber is treated according to the methods described herein. In certain other embodiments, both of the distal and proximal end faces of the fiber are treated. Generally, the method 1000 begins at operation 1010 and FIG. 11A, wherein a mask 1130 is applied to a surface area of the end face 1111 corresponding to a cross-section of at least a core (core 502 is shown in FIG. 11C), and in certain embodiments, an inner cladding (e.g., inner cladding 503) of the fiber. For example, the mask 1130 may have a diameter that is substantially the same or larger than a diameter of the core 302 or the inner cladding 503. In certain embodiments, the mask 1130 comprises an adhesive, such as a UV-adhesive or epoxy, that is cured upon application to the end face 1111 by exposing the mask 1130 to UV light. Prior to application of the mask 1130, the end face 1111 may be flat polished to facilitate better adhesion of the mask 1130 and/or form a more specular surface for optimal propagation of the laser light beam 113 to or from the core 502.

At operation 1020 and FIG. 11B, the masked end face 1111 is exposed to a particle abrasion process, such as a sand-blasting process utilizing aluminum oxide ($AlO_2$) particles having diameters of between about 10 μm and about 20 μm, such as about 12 μm. As a result, an exposed surface area of the end face 1111, e.g., the surface area of the end face 1111 corresponding to the cross-section of the outer cladding (e.g., outer cladding 304) and coating (e.g., coating 306) of the fiber is at least partially roughened or coarsened by the particle abrasion process (represented as hatch marks 1120 in FIG. 11B), while the surface area protected by the mask 1130, e.g., the surface area corresponding to the cross-section of the core of the fiber, is unaffected. The amount of illumination light scattering caused by the end face 1111 is correlated to the level or degree of roughness thereof. Thus, increasing the time of exposure to the particle abrasion process or increasing the velocity of the particles abrading the end face 1111 may increase the amount of illumination light scattering caused by end face 1111. As previously described, in embodiments where both distal and proximal end faces of the fiber are treated, the degree of roughness may be varied for each of the proximal and distal end. For example, the proximal end may be roughened relatively lightly while the distal end is roughened relatively heavily, or vice-versa. The difference in level of roughness between end faces may facilitate higher angular spread of illumination light as compared to having a single roughened end face or having two end faces with similar roughness levels.

After the particle abrasion process, the mask 1130 is removed and the end face 1111 is cleaned at operation 1030 and FIG. 11C. For example, the end face 1111 is exposed to an ultrasonic cleaning process utilizing an alcohol solution to remove the mask 1130 and clean the end face 1111. The resulting end face 1111 includes a substantially planar surface area corresponding to the cross-section of at least the core of the fiber, and a roughened surface area (represented as hatch marks 1120 in FIG. 11C) corresponding to the cross-section of at least the outer cladding.

As noted earlier, the end faces of a fiber may be treated at least one of two ways to increase the illumination output angle of an optical fiber cable. In addition to being exposed to a roughening process as described with reference to FIGS. 7-11C, one or more end faces of the fiber may be angled or beveled by a polishing process to increase the illumination light scattering characteristics of the optical fiber.

Figure 12A:
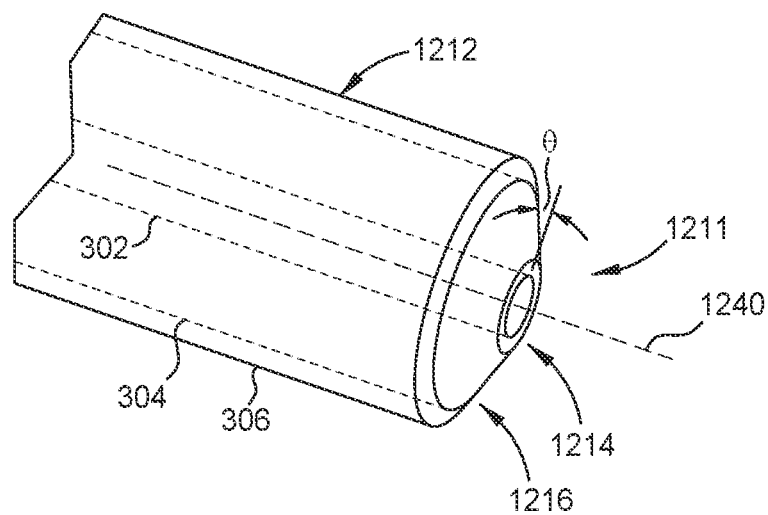
FIGS. 12A-12B illustrate different views of a fiber, in accordance with certain embodiments of the present disclosure.
Figure 12B:
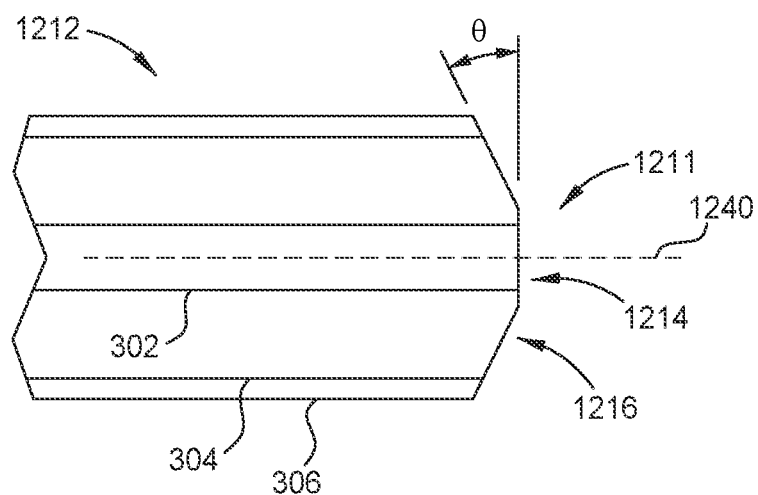

FIGS. 12A and 12B illustrate a perspective view and a partial cross-sectional view, respectively, of a beveled end 1212 of a fiber having a substantially frustoconical end face 1211, in accordance with certain embodiments of the present disclosure. The end 1212 may be a distal or proximal end of the fiber 300, which is exposed to an angled polishing process to increase an illumination light output angle of the fiber. The end 1212, similar to the portion 311 depicted in FIG. 4, includes core 302 circumferentially surrounded by outer cladding 304, and the outer cladding 304 is circumferentially surrounded by coating 306. A surface area 1214 of the end face 1211 corresponding to a cross-section of at least the core 302 is planar and substantially orthogonal relative to a central axis 1240 of the end 1212. In certain embodiments, the planar surface area 1214 of the end 1212 corresponds to an entire cross-section of the core 302, as well as a portion of a cross-section of the outer cladding 304. For example, the planar surface area 1214 of the end 1212 may have a diameter substantially the same or greater than a diameter of the core 302, such as a diameter between about 20% and about 40% greater than a diameter of the core 302.

A surface area 1216 of the end face 1211 corresponding to a cross-section of the outer cladding 304, on the other hand, is angled relative to the planar surface area 1214. The angled surface area 1216 is disposed at an angle Θ relative to the planar surface area 1214. In certain embodiments, the angle Θ is between about 0° and about 20° relative to the planar surface area 1214. In certain other embodiments, the angle Θ is between about 60° and about 80° relative to the planar surface area 1214. Other angles are also contemplated (e.g., the angle Θ may be between about 20° and about 60° relative to the surface area 1314). Together, the planar surface area 1214 and the angled surface area 1216 form the frustoconical shape of the end face 1211.

The beveled structure of the end 1212 functions similarly to the roughened surface areas described above with reference to FIGS. 7-11C and increases the illumination light output angle of the fiber. As described above, laser light, such as laser light beam 113, is transmitted into or out of the core 302 through planar surface area 1214 of the end face 1211, thus remaining unaffected by the beveled structure of the end 1212. Illumination light, such as illumination light beam 150, however, is transmitted into or out of both the core 302 and outer cladding 304. Illumination light passing through the outer cladding 304 is thus refracted by the angled surface area 1216, which increases the angular spread of the illumination light at end face 1211 as compared to a planar end face surface. The increased angular spread of the illumination light at end face 1211 results in an overall increased illumination light output angle of the fiber. Accordingly, the illumination light output angle of the fiber can be modulated by increasing or decreasing the angle of surface area 1216 relative to surface area 1214, all the while preserving laser beam quality. In certain embodiments, the illumination light output angle of a fiber having at least one beveled end 1212 is increased between about 0.05 NA and about 0.25 NA, such as between about 0.1 and about 0.2 NA, as compared to a fiber having two planar (e.g., completely flat) end faces.

Figure 13:
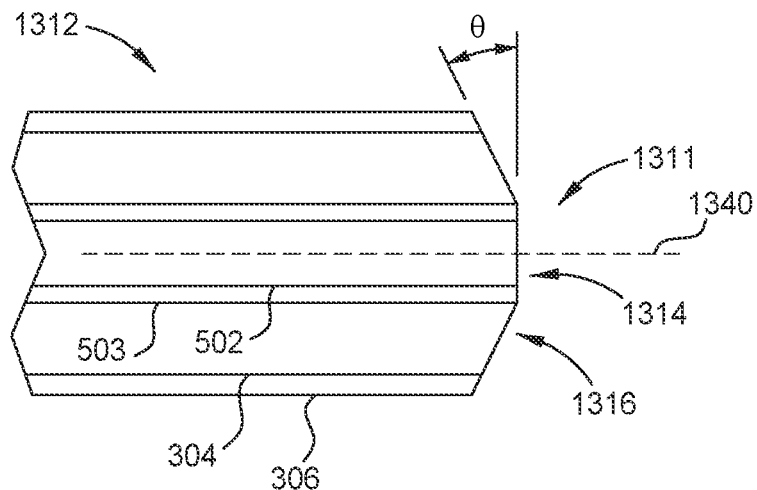
FIG. 13 illustrates a side cross-sectional view of a fiber with an inner cladding, in accordance with certain embodiments of the present disclosure.

FIG. 13 illustrates a partial cross-sectional view of another beveled end 1312 of a fiber having an angled end face 1311 to increase an illumination output angle of the fiber, in accordance with certain embodiments of the present disclosure. The end face 1311 may be a distal or proximal end face of the fiber 500 depicted in FIG. 5, and includes inner cladding 503 circumferentially surrounding core 502, outer cladding 304 circumferentially surrounding the inner cladding 503, and coating 306 circumferentially surrounding the outer cladding 304. A surface area 1314 of the end face 1311 corresponding to a cross-section of at least the core 502 and the inner cladding 503 is planar and substantially orthogonal relative to a central axis 1340 of the end 1312. In certain embodiments, the planar surface area 1314 of the end 1312 corresponds to an entire cross-section of the core 502 and the inner cladding 503, as well as a portion of a cross-section of the outer cladding 304. For example, the planar surface area 1314 may have a diameter substantially the same or greater than a diameter of the inner cladding 503, such as a diameter between about 20% and about 40% greater than a diameter of the inner cladding 503.

A surface area 1316 of the end face 1311 corresponding to a cross-section of the outer cladding 304 and/or the coating 306 is disposed at angle Θ relative to the surface area 1314. In certain embodiments, the angle Θ is between about 0° and about 20° relative to the surface area 1314. In certain other embodiments, the angle Θ is between about 60° and about 80° relative to the surface area 1314. Other angles are also contemplated (e.g., the angle Θ may be between about 20° and about 60° relative to the surface area 1314). The angle of the surface area 1316 functions to modulate the angular spread of illumination light 150 passing therethrough.

Although depicted as specular surfaces in FIGS. 12A-13, in certain embodiments, the angled surface areas 1216 and 1316 are roughened (e.g., using the techniques described above) to further increase the angular spread of illumination light 150 passing therethrough. In certain embodiments, the angled surface areas 1216 and 1316 are non-linear in truncation (e.g., a cross-section of the beveled end faces 1211 and 1311 includes non-linear edges for surfaces areas 1216 and 1316). For example, in certain embodiments, the angled surface areas 1216, 1316 are wavy or undulating in morphology for greater angular spread of illumination light 150 passing therethrough.

Figure 14:
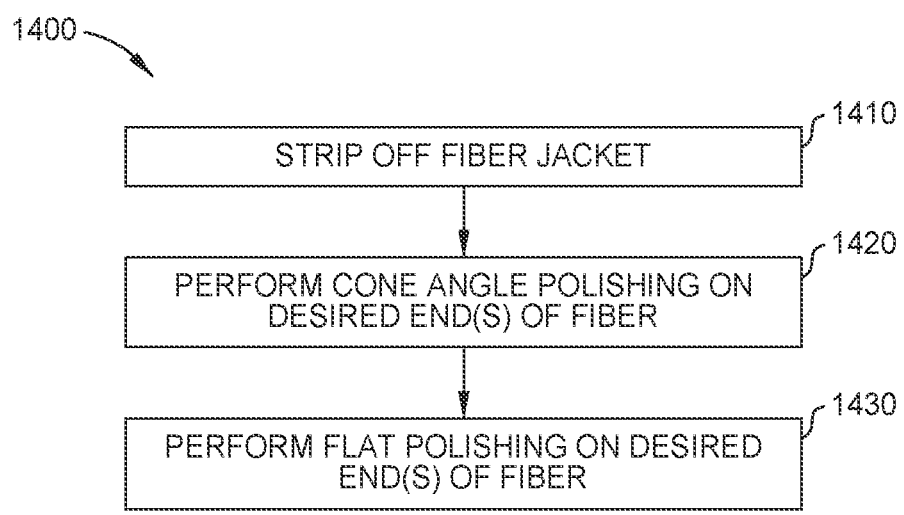
FIG. 14 illustrates a flow diagram of a method of forming a fiber, in accordance with certain embodiments of the present disclosure.
Figure 15A:
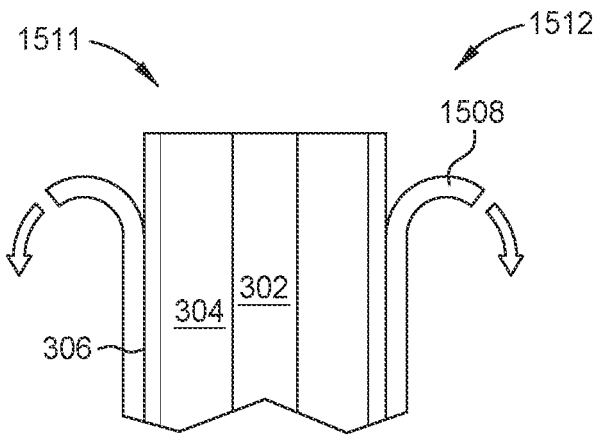
FIGS. 15A-15C illustrate different states of a fiber at different operations of the method of FIG. 14, in accordance with certain embodiments of the present disclosure.
Figure 15B:
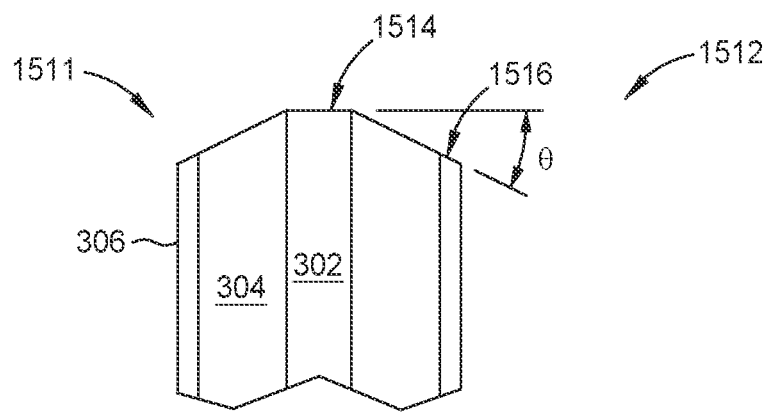
Figure 15C:
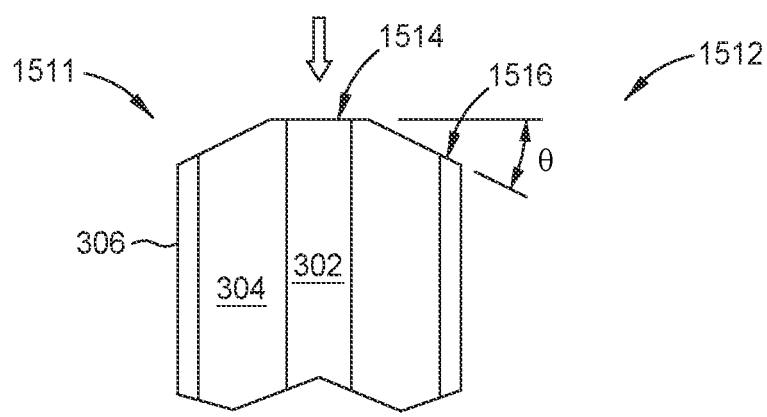

FIG. 14 illustrates a flow diagram of a method 1400 for polishing an end of a fiber to form a beveled end face and increase an illumination light output angle thereof, in accordance with certain embodiments of the present disclosure. FIGS. 15A-15C schematically illustrate cross-sectional views of an end 1512 of a fiber at different stages of the method 1400 represented in FIG. 14. Therefore, FIGS. 14 and 15A-15C are herein described together for clarity.

The method 1400 may be utilized to form the ends 1212 and 1312 having end faces 1211, 1311 described above. In certain embodiments, only one of the distal or proximal end faces of the fiber is polished according to the methods described herein. In certain other embodiments, both of the distal and proximal end faces of the fiber are polished. Generally, the method 1400 begins at operation 1410 and FIG. 15A, wherein a jacket 1508, such as buffer 308, is stripped from the fiber (end 1512 of the fiber is shown in FIG. 15A). In certain examples, the jacket 1508 is formed of plastic, such as ETFE.

At operation 1420 and FIG. 15B, the end 1512 is polished along a circumferential edge of end face 1511 to form an angled surface area 1516. The polishing process at operation 1420 is performed at one or more desired angles to form the angled surface area 1516 having at least an angle Θ relative to a planar top surface area 1514. Together, the planar surface area 1514 and the angled surface area 1516 may form the beveled shape of the end face 1511. In certain embodiments, the polishing process is performed at multiple desired angles to form an angled surface area 1516 having a nonlinear taper, as described above. Increasing the nonlinearity of the angled surface area 1516 may increase the amount of illumination light scattering caused thereby, and thus, the degree of angular spread at end face 1511 may be modulated by modifying the linearity (e.g., number of angles relative to the surface area 1514) of the surface area 1516.

In some examples, the angled surface area 1516 is polished to have an angle Θ between about 0° and about 20° relative to the planar surface area 1514. In some examples, the angled surface area 1516 is polished to have an angle Θ between about 60° and about 80° relative to the planar surface area 1514. Other angles are also contemplated (e.g., the angle Θ may be between about 20° and about 60° relative to the planar surface area 1514). In embodiments where both distal and proximal ends of the fiber are beveled, the number and degree of angles may be varied for each of the proximal and distal ends. The differences in beveling between ends may facilitate even higher angular spread of illumination light emitted by the fiber.

Upon formation of the angled surface area 1516, the planar surface area 1514 of the end 1512 is polished and cleaned using a flat polishing process at operation 1430 and FIG. 15C. The flat polishing process ensures specularity of the planar surface area 1514, and further ensures the planar surface area 1514 encompasses at least an entire cross-section of the core 302, thus preserving quality of the laser light beam 113 emitted therefrom. Generally, the polishing processes at operation 1430 may be performed utilizing the same polishing system as used for operation 1420, such as a mechanical fiber polisher having a polishing platen or plate. The resulting end face 1511 includes a substantially planar surface area 1514 corresponding to the cross-section of at least the core 302 of the fiber, and an angled surface area 1516 corresponding to the cross-section of at least the outer cladding 304.

As described above, an optical fiber cable is capable of transmitting both a laser light beam through a core, and illumination light through the core and an outer cladding. The optical fiber cable does not have two separate fibers for illumination light and the laser light beam, but rather one fiber that includes a core to transmit the laser light beam, and the core and an outer cladding to transmit the illumination light. The optical fiber cable can be used in a system for medical procedures, and the system provides both laser light beam for the cauterizing or burning, and illumination light to aid the user in performance of the procedure.

The use of a combined core and outer cladding to transmit both the laser light beam and illumination light results in a more compact fiber, and removes the need for adhering two fibers together. The narrower fiber is useful for medical procedures that require thinner probe tips. In addition, the optical fiber cable is more thermally stable than a traditional optical fiber cable, due to the lack of thermally unstable adhesive. The use of a single fiber in the optical fiber cable removes the need for two connectors (one for each fiber), and thus only one connector is necessary, which reduces the manufacturing and labor costs, as there is no need to handle assembly of two fibers.

Furthermore, treating surface areas corresponding to the outer cladding on one or both end faces of the fiber enables a compact fiber having a large illumination output angle while maintaining laser beam performance of the fiber. One or both end faces of the fiber are treated by a roughening or polishing process to form a roughened or angled surface around the core. The roughened or angled surfaces increase the angular spread of illumination light transmitted therethrough without affecting transmission of the laser light beam to or from the core, thus causing the increased illumination output angle of the fiber without impairing laser efficiency. Accordingly, the single compact fiber may be utilized for medical procedures requiring larger illumination spreading angles.

EXAMPLE EMBODIMENTS

Embodiment 1: A surgical laser system, comprising: an illumination light source configured to emit an illumination light onto a focusing lens; a laser light source configured to emit a laser light beam onto the focusing lens; the focusing lens configured to: focus the illumination light onto a core and an outer cladding of a fiber coupled to the surgical laser system; and focus the laser light beam onto the core of the fiber, wherein the fiber is downstream from the focusing lens, the fiber comprising: a proximal end face at a proximal end of the fiber, the proximal end being coupled to the surgical laser system; a distal end face at a distal end of the fiber, the distal end being coupled to a laser probe assembly; the core configured to transmit the illumination light and the laser light beam; and the outer cladding circumferentially surrounding the core and configured to transmit the illumination light, wherein at least a surface area of the proximal end face or the distal end face corresponding to the outer cladding is roughened.

Embodiment 2: The surgical laser system of Embodiment 1 described above, wherein the roughened surface area comprises at least 50% of a total area of the proximal end face or the distal end face of the fiber.

Embodiment 3: The surgical laser system of Embodiment 2 described above, wherein the roughened surface area comprises at least 80% of a total area of the proximal end face or the distal end face of the fiber.

Embodiment 4: The surgical laser system of Embodiment 1 described above, wherein the surface area of each of the proximal end face and the distal end face corresponding to the outer cladding is roughened.

Embodiment 5: The surgical laser system of Embodiment 4 described above, wherein the roughened surface area of the proximal end face has a different level of roughness than the roughened surface area of the distal end face.

Embodiment 6: The surgical laser system of Embodiment 1 described above, wherein the fiber further comprises an inner cladding disposed between the core and the outer cladding.

Embodiment 7: The surgical laser system of Embodiment 1 described above, wherein a surface area of the proximal end face and the distal end face corresponding to the core is not roughened.

Embodiment 8: A laser probe assembly, comprising: a probe body shaped and sized for grasping by a user; and a probe tip housing a fiber having a proximal end face and a distal end face opposite the proximal end face, the fiber further comprising: a core configured to transmit a laser light beam and an illumination light; an outer cladding circumferentially surrounding the core and configured to transmit the illumination light, wherein at least a surface area of the proximal end face or the distal end face corresponding to the outer cladding is angled relative to a planar surface area corresponding to the core; and a coating circumferentially surrounding the outer cladding.

Embodiment 9: The laser probe assembly of Embodiment 8 described above, wherein the angled surface area is disposed at an angle between about 0° and about 30° relative to the planar surface area.

Embodiment 10: The laser probe assembly of Embodiment 8 described above, wherein the angled surface area is disposed at an angle between about 30° and about 60° relative to the planar surface area.

Embodiment 11: The laser probe assembly of Embodiment 8 described above, wherein the angled surface area is disposed at an angle between about 60° and about 90° relative to the planar surface area.

Embodiment 12: The laser probe assembly of Embodiment 8 described above, wherein the angled surface area comprises a nonlinear taper.

Embodiment 13: The laser probe assembly of Embodiment 8 described above, wherein the angled surface area is further roughened.

Embodiment 14: The laser probe assembly of Embodiment 8 described above, wherein the fiber further comprises an inner cladding disposed between the core and the outer cladding.

Embodiment 15: A fiber, comprising: a proximal end face at a proximal end of the fiber; a distal end face at a distal end of the fiber; a core configured to transmit a laser light beam and an illumination light; an outer cladding circumferentially surrounding the core and configured to transmit the illumination light, wherein at least a surface area of the proximal end face or the distal end face corresponding to the outer cladding is angled relative to a planar surface area corresponding to the core; and a coating circumferentially surrounding the outer cladding.

Embodiment 16: The fiber of Embodiment 15 described above, wherein the angled surface area is disposed at an angle between about 0° and about 30° relative to the planar surface area.

Embodiment 17: The fiber of Embodiment 15 described above, wherein the angled surface area is disposed at an angle between about 30° and about 60° relative to the planar surface area.

Embodiment 18: The fiber of Embodiment 15 described above, wherein the angled surface area is disposed at an angle between about 60° and about 90° relative to the planar surface area.

Embodiment 19: The fiber of Embodiment 15 described above, wherein the angled surface area comprises a nonlinear taper.

Embodiment 20: The fiber of Embodiment 15 described above, wherein the angled surface area is further roughened.

Embodiment 21: The fiber of Embodiment 15 described above, wherein the fiber further comprises an inner cladding disposed between the core and the outer cladding.

Embodiment 22: A surgical laser system, comprising: an illumination light source configured to emit an illumination light onto a focusing lens; a laser light source configured to emit a laser light beam onto the focusing lens; the focusing lens configured to: focus the illumination light onto a core and an outer cladding of a fiber coupled to the surgical laser system; and focus the laser light beam onto the core of the fiber, wherein the fiber is downstream from the focusing lens, the fiber comprising: a proximal end face at a proximal end of the fiber, the proximal end being coupled to the surgical laser system; a distal end face at a distal end of the fiber, the distal end being coupled to a laser probe assembly; the core configured to transmit the illumination light and the laser light beam; and the outer cladding circumferentially surrounding the core and configured to transmit the illumination light, wherein at least a surface area of the proximal end face or the distal end face corresponding to the outer cladding is angled relative to a planar surface area corresponding to the core.

Embodiment 23: The surgical laser system of Embodiment 22 described above, wherein the angled surface area is disposed at an angle between about 0° and about 30° relative to the planar surface area.

Embodiment 24: The surgical laser system of Embodiment 22 described above, wherein the angled surface area is disposed at an angle between about 30° and about 60° relative to the planar surface area.

Embodiment 25: The surgical laser system of Embodiment 22 described above, wherein the angled surface area is disposed at an angle between about 60° and about 90° relative to the planar surface area.

Embodiment 26: The surgical laser system of Embodiment 22 described above, wherein the angled surface area comprises a nonlinear taper.

Embodiment 27: The surgical laser system of Embodiment 22 described above, wherein the angled surface area is further roughened.

Embodiment 28: The surgical laser system of Embodiment 22 described above, wherein the fiber further comprises an inner cladding disposed between the core and the outer cladding.

Embodiment 29: A method of forming an optical fiber, the optical fiber comprising: a proximal end face at a proximal end of the fiber; a distal end face at a distal end of the fiber; a core configured to transmit a laser light beam and an illumination light; an outer cladding circumferentially surrounding the core and configured to transmit the illumination light; and a coating circumferentially surrounding the outer cladding; the method comprising: applying a mask to a surface area of the proximal end face or the distal end face of the fiber corresponding to the core; exposing the masked end face to a particle abrasion process to roughen at least a surface area of the masked end face corresponding to the outer cladding; and, cleaning the masked end face to remove the mask.

Embodiment 30: The method of Embodiment 29 described above, wherein the roughened surface area comprises at least 50% of a total area of the proximal end face or the distal end face of the fiber.

Embodiment 31: The method of Embodiment 30 described above, wherein the roughened surface area comprises at least 80% of a total area of the proximal end face or the distal end face of the fiber.

Embodiment 32: The method of Embodiment 29 described above, wherein the surface area of each of the proximal end face and the distal end face corresponding to the outer cladding is roughened.

Embodiment 33: The method of Embodiment 32 described above, wherein the roughened surface area of the proximal end face has a different level of roughness than the roughened surface area of the distal end face.

Embodiment 34: The method of Embodiment 29 described above, wherein the fiber further comprises an inner cladding disposed between the core and the outer cladding.

Embodiment 35: The method of Embodiment 29 described above, wherein a surface area of the proximal end face and the distal end face corresponding to the core is not roughened.

Embodiment 36: A method of forming an optical fiber, the optical fiber comprising: a proximal end face at a proximal end of the fiber; a distal end face at a distal end of the fiber; a core configured to transmit a laser light beam and an illumination light; an outer cladding circumferentially surrounding the core and configured to transmit the illumination light; and a coating circumferentially surrounding the outer cladding; the method comprising: exposing a circumferential edge of the proximal end face or the distal end face to an angled polishing process to form a surface area corresponding to the outer cladding that is angled relative to a planar surface area corresponding to the core; and, exposing the planar surface area to a flat polishing process.

Embodiment 37: The method of Embodiment 36 described above, wherein the angled surface area is disposed at an angle between about 0° and about 30° relative to the planar surface area.

Embodiment 38: The method of Embodiment 36 described above, wherein the angled surface area is disposed at an angle between about 30° and about 60° relative to the planar surface area.

Embodiment 39: The method of Embodiment 36 described above, wherein the angled surface area is disposed at an angle between about 60° and about 90° relative to the planar surface area.

Embodiment 40: The method of Embodiment 36 described above, wherein the angled surface area comprises a nonlinear taper.

Embodiment 41: The method of Embodiment 36 described above, wherein the angled surface area is further roughened.

Embodiment 42: The method of Embodiment 36 described above, wherein the fiber further comprises an inner cladding disposed between the core and the outer cladding.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A laser probe assembly, comprising:
   a probe body shaped and sized for grasping by a user; and
   a probe tip housing a fiber having a proximal end face and
      a distal end face opposite the proximal end face, the fiber further comprising:
      a core configured to transmit a laser light beam and an illumination light;
      an outer cladding circumferentially surrounding the core and configured to transmit the illumination light, wherein at least a surface area of the proximal end face or the distal end face corresponding to the outer cladding is roughened; and
      a coating circumferentially surrounding the outer cladding;
   wherein the roughened surface area comprises at least 50% of a total area of the proximal end face or the distal end face of the fiber.

2. The laser probe assembly of claim 1, wherein the roughened surface area comprises at least 80% of a total area of the proximal end face or the distal end face of the fiber.

3. A laser probe assembly, comprising:
   a probe body shaped and sized for grasping by a user; and
   a probe tip housing a fiber having a proximal end face and
      a distal end face opposite the proximal end face, the fiber further comprising:
      a core configured to transmit a laser light beam and an illumination light;
      an outer cladding circumferentially surrounding the core and configured to transmit the illumination light, wherein at least a surface area of the proximal end face or the distal end face corresponding to the outer cladding is roughened; and
      a coating circumferentially surrounding the outer cladding;
   wherein the surface area of each of the proximal end face and the distal end face corresponding to the outer cladding is roughened.

4. The laser probe assembly of claim 3, wherein the roughened surface area of the proximal end face has a different level of roughness than the roughened surface area of the distal end face.

5. A fiber, comprising:
   a proximal end face at a proximal end of the fiber;
   a distal end face at a distal end of the fiber;
   a core configured to transmit a laser light beam and an illumination light;
   an outer cladding circumferentially surrounding the core and configured to transmit the illumination light, wherein at least a surface area of the proximal end face or the distal end face corresponding to the outer cladding is roughened; and
   a coating circumferentially surrounding the outer cladding;
   wherein the roughened surface area comprises at least 50% of a total area of the proximal end face or the distal end face of the fiber.

6. The fiber of claim 5, wherein the roughened surface area comprises at least 80% of a total area of the proximal end face or the distal end face of the fiber.

7. A fiber, comprising:
- a proximal end face at a proximal end of the fiber;
- a distal end face at a distal end of the fiber;
- a core configured to transmit a laser light beam and an illumination light;
- an outer cladding circumferentially surrounding the core and configured to transmit the illumination light, wherein at least a surface area of the proximal end face or the distal end face corresponding to the outer cladding is roughened; and
- a coating circumferentially surrounding the outer cladding;

wherein the surface area of each of the proximal end face and the distal end face corresponding to the outer cladding is roughened.

8. The fiber of claim 7, wherein the roughened surface area of the proximal end face has a different level of roughness than the roughened surface area of the distal end face.

* * * * *